US012758303B2

(12) United States Patent
May et al.

(10) Patent No.: US 12,758,303 B2
(45) Date of Patent: Oct. 13, 2026

(54) MICROWAVE ABLATION PROBE TIP

(71) Applicant: Varian Medical Systems, Inc., Palo Alto, CA (US)

(72) Inventors: Justin May, Austin, TX (US); Virgilio Gomez, Kyle, TX (US); Paul Joseph Hattan, Minneapolis, MN (US)

(73) Assignee: Varian Medical Systems, Inc., Palo Alto, CA (US)

( * ) Notice: Subject to any disclaimer, the term of this patent is extended or adjusted under 35 U.S.C. 154(b) by 187 days.

(21) Appl. No.: 18/778,252

(22) Filed: Jul. 19, 2024

(65) Prior Publication Data

US 2026/0020900 A1 Jan. 22, 2026

(51) Int. Cl.
*A61B 18/14* (2006.01)
*A61B 18/18* (2006.01)

(52) U.S. Cl.
CPC .. *A61B 18/1477* (2013.01); *A61B 2018/1869* (2013.01)

(58) Field of Classification Search
CPC ........................ A61B 18/1815; A61B 18/1477
See application file for complete search history.

(56) References Cited

U.S. PATENT DOCUMENTS

| | | | | |
|---|---|---|---|---|
| 2008/0275436 | A1* | 11/2008 | Cronin | A61B 18/18 606/33 |
| 2016/0262832 | A1* | 9/2016 | Cronin | G06T 7/30 |
| 2020/0138514 | A1* | 5/2020 | Blumenkranz | A61B 18/1815 |
| 2022/0160426 | A1* | 5/2022 | Eaton-Evans | A61B 18/1815 |
| 2022/0361947 | A1* | 11/2022 | Wang | A61B 18/1815 |

* cited by examiner

*Primary Examiner* — Sean W Collins
(74) *Attorney, Agent, or Firm* — Morgan, Lewis & Bockius LLP; Manita Rawat

(57) ABSTRACT

A microwave ablation probe tip includes a post portion configured to be received in an ablation probe needle, the post portion comprising one or more annular grooves, and an insertion portion comprising a shoulder at which the insertion portion is connected to the post portion, wherein the insertion portion tapers in a direction away from the shoulder.

15 Claims, 5 Drawing Sheets

MICROWAVE ABLATION PROBE TIP

TECHNICAL FIELD

The disclosure relates to tips used in microwave ablation probes.

BACKGROUND

Microwave ablation probes can be used in clinical treatments such as thermal ablation treatments. In such treatments, thermal ablation can be used to destroy undesirable tissue such as malignant cells in a body. A microwave ablation antenna can be included in the probe and be used to deliver Radio Frequency (RF) energy such as microwave energy to a target tissue to heat the target tissue and destroy the target tissue. The microwave ablation antenna can be positioned inside the ablation probe that can position the microwave ablation antenna proximate the target tissue.

In some treatments, the ablation probe is guided to the target tissue though other tissue or near to tissues or body structures that it is desirable not to damage during treatment. It is desirable, therefore, to maintain a small size of the microwave ablation antenna and/or the needle of the probe. In this manner, damage to tissues and other body structures that may be located close to the target tissue to be destroyed is minimized or prevented. It can be difficult to manufacture ablation probes that have suitably sized for thermal ablation due to the complexity of such devices and the need to position all elements so that an ablation zone can be repeatably achieved. There exists a need, therefore, for improved microwave ablation probes or needle designs that are sufficiently small, deliver known and repeatable ablation zones and can be manufactured with high quality and low cost.

SUMMARY

The present disclosure is directed to microwave ablation probes that may include an improved tip design over existing probes. The tips of the ablation probes of the present disclosure may include features to ensure that the tip may be robustly attached at the distal end of the needle. The tips of the present disclosure may also have self-centering features to ensure that tip is accurately position in the end of the needle. Still further, the tips of the present disclosure may include protective features to prevent fouling or inadvertent interference with neighboring elements inside the needle. The tip may also be formed from a ceramic material in an injection molding process. Such features are not found in existing microwave ablation probes. The probe tips of the present disclosure result in microwave ablation probes that do have performance issues that may arise from inadvertent manufacturing defects that may be difficult to detect in some instances.

In accordance with some embodiments, a microwave ablation probe is provided. The microwave ablation probe may include a post portion configured to be received in an ablation probe needle, the post portion comprising one or more annular grooves, and an insertion portion that includes a shoulder at which the insertion portion is connected to the post portion, wherein the insertion portion tapers in a direction away from the shoulder.

In one aspect, each of the one or more annular grooves may extend circumferentially around an outer surface of the post portion.

In another aspect, the one or more annular grooves may include a first groove, a second groove, and a third groove axially spaced apart from each other.

In another aspect, the insertion portion may include a seating surface configured to contact an end surface of the ablation probe needle and the seating surface may be angled relative to the end surface of the ablation probe needle.

In another aspect, the seating surface may be angled in a direction away from the post portion.

In another aspect, the seating surface may be positioned radially outward of an outer surface of the post portion.

In another aspect, the insertion portion terminates at a point.

In another aspect, the insertion portion may include a conical shape.

In another aspect, the post portion may include a center bore.

In another aspect, the tip may include a tube positioned in the center bore and extending out of the center bore in a direction away from the insertion portion.

In another aspect, the tube may be configured to receive a microwave antenna therein.

In some embodiments of the present disclosure, a microwave ablation probe is provided. The microwave ablation probe may include a shell defining an axially extending inner cavity, a cable positioned in the inner cavity and comprising a microwave antenna, and a tip connected at a distal end of the shell. The tip may include a post portion received inside the distal end of the shell and an insertion portion connected to the post portion and extending away from the distal end of the shell. The post portion may include one or more annular grooves.

In one aspect, the tip may include a seating surface contacting the end surface of the distal end of the shell, and the seating surface may be oriented at an oblique angle relative to an axis of the shell.

In another aspect, the seating surface may be angled in a direction away from the post portion.

In another aspect, the insertion portion may include a tapered outer surface terminating at a point.

In another aspect, the post portion may include a center bore.

In another aspect, the probe may include a ferrule positioned over the antenna. The ferrule may extend in an axial direction from the antennae and at least a portion of the ferrule received inside the center bore.

In another aspect, the tip may include a tube positioned in the center bore and extend out of the center in a direction away from the insertion portion, the at least a portion of the ferrule positioned inside the tube.

In another aspect, the post portion and the insertion portion may be integrally formed from a ceramic material using an injection molding process.

In another aspect, the post portion and the insertion portion of the tip may be integrally formed from a ceramic material using an injection molding process.

In some embodiments of the present disclosure, a microwave ablation apparatus is provided. The microwave ablation apparatus may include an ablation console comprising a microwave generator, and a microwave ablation probe. The microwave ablation probe may include a shell defining an axially extending inner cavity, a cable positioned in the inner cavity that includes a microwave antenna; and a tip connected at a distal end of the shell. The tip may include a post portion received inside the distal end of the shell and an insertion portion connected to the post portion and extending away from the distal end of the shell. The post portion including one or more annular grooves.

Further areas of applicability will become apparent from the description provided herein. The description and specific examples in this summary are intended for purposes of illustration only and are not intended to limit the scope of the present disclosure.

BRIEF DESCRIPTION OF THE DRA WINGS

The features and advantages of the present disclosures will be more fully disclosed in, or rendered apparent by the following detailed descriptions of example embodiments. The detailed descriptions of the example embodiments are to be considered together with the accompanying drawings wherein like numbers refer to like parts and further wherein.

DETAILED DESCRIPTION

Figure 1:
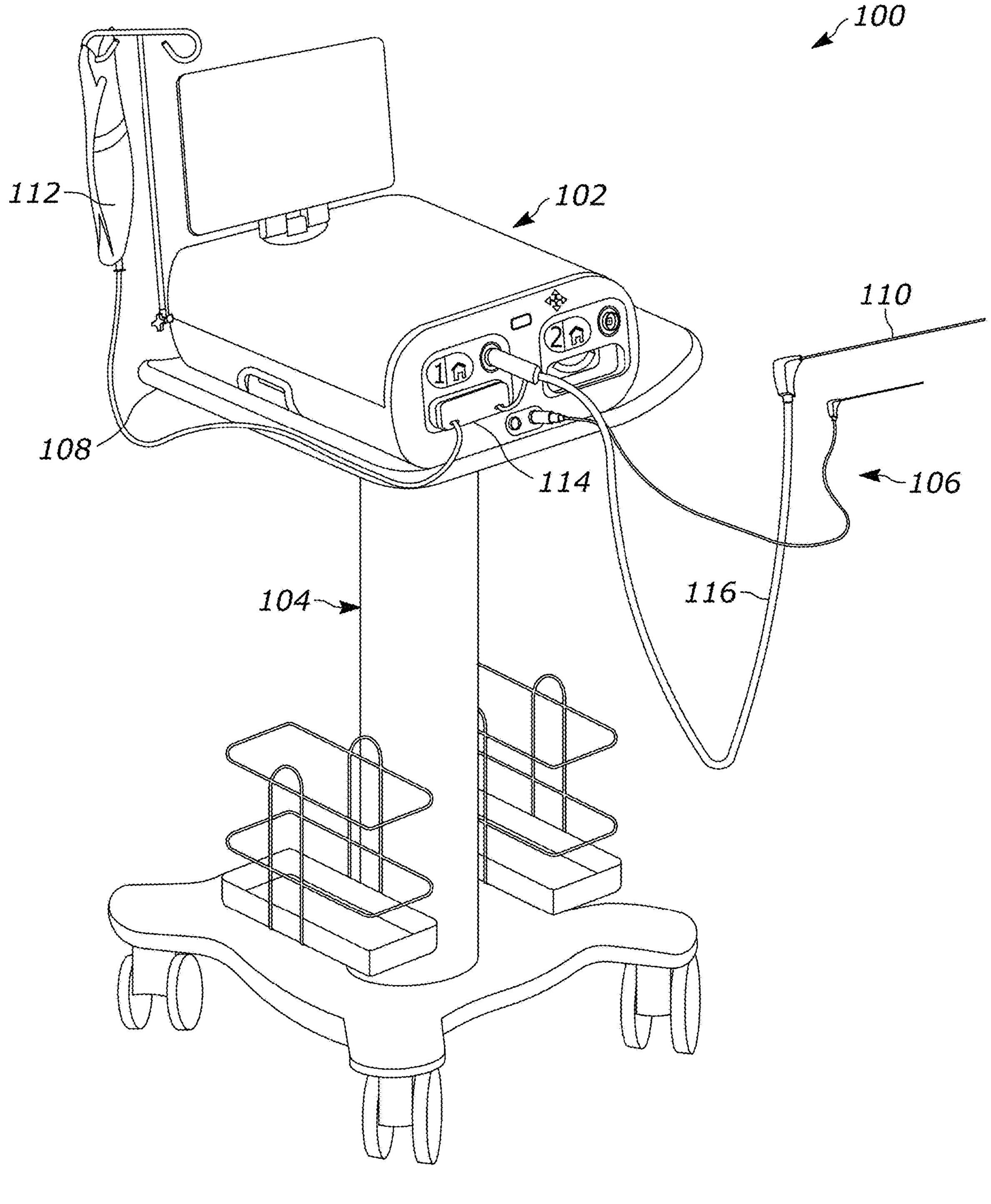
FIG. 1 is an isometric view of an example microwave ablation apparatus in accordance with some embodiments of the present disclosure.

The description of the preferred embodiments is intended to be read in connection with the accompanying drawings, which are to be considered part of the entire written description of these disclosures. While the present disclosure is susceptible to various modifications and alternative forms, specific embodiments are shown by way of example in the drawings and will be described in detail herein. The objectives and advantages of the claimed subject matter will become more apparent from the following detailed description of these exemplary embodiments in connection with the accompanying drawings.

It should be understood, however, that the present disclosure is not intended to be limited to the particular forms disclosed. Rather, the present disclosure covers all modifications, equivalents, and alternatives that fall within the spirit and scope of these exemplary embodiments. The terms "couple," "coupled," "operatively coupled," "operatively connected," and the like should be broadly understood to refer to connecting devices or components together either mechanically, electrically, wired, wirelessly, or otherwise, such that the connection allows the pertinent devices or components to operate (e.g., communicate) with each other as intended by virtue of that relationship.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to +10% of the recited value, inclusive. For example, the phrase "about 8" preferably refers to a value of 7.2 to 8.8, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

Turning now to FIG. 1, an example microwave ablation apparatus 100 is shown. In this example, the ablation apparatus 100 includes an ablation console 102, and an ablation probe 110. The ablation console 102 may be portable, in some examples, and may be positioned on a platform 108 of stand 104 to allow the console 102 to be easily moved and positioned as desired during treatment. The console 102 may include a microwave generator that may provide a power signal that is sent to an antenna in the needle of the ablation probe 110. The power signal may be provided to the antenna via a supply cable 116 that may extend from the console 102 to the ablation probe 110. The supply cable 116 may also provide a coolant to the ablation probe 110. The coolant may be a saline solution or other coolant that may be supplied to the ablation probe 110 from a coolant receptacle 112 via a pump cartridge 114 or other pump mechanism.

During an ablation treatment, the needle of the ablation probe 110 may be positioned at or near a target tissue in a patient. A power signal may be supplied to the ablation probe 110 from the console 102. The power signal may be supplied to the ablation probe 110 via the supply cable 116. The power signal may cause microwaves to be emitted from an antenna in the needle of the ablation probe 110. The microwaves may cause the tissue at the needle to be heated to a suitable temperature to destroy the target tissue. A temperature sensor 106 may be positioned at or near the target tissue to measure a temperature that may be achieved at or near the ablation zone. In addition and as further described below, the needle or the handle of the ablation probe 110 may include other thermocouples or temperature probes to provide information regarding temperatures of the coolant or the needle.

Figure 2:
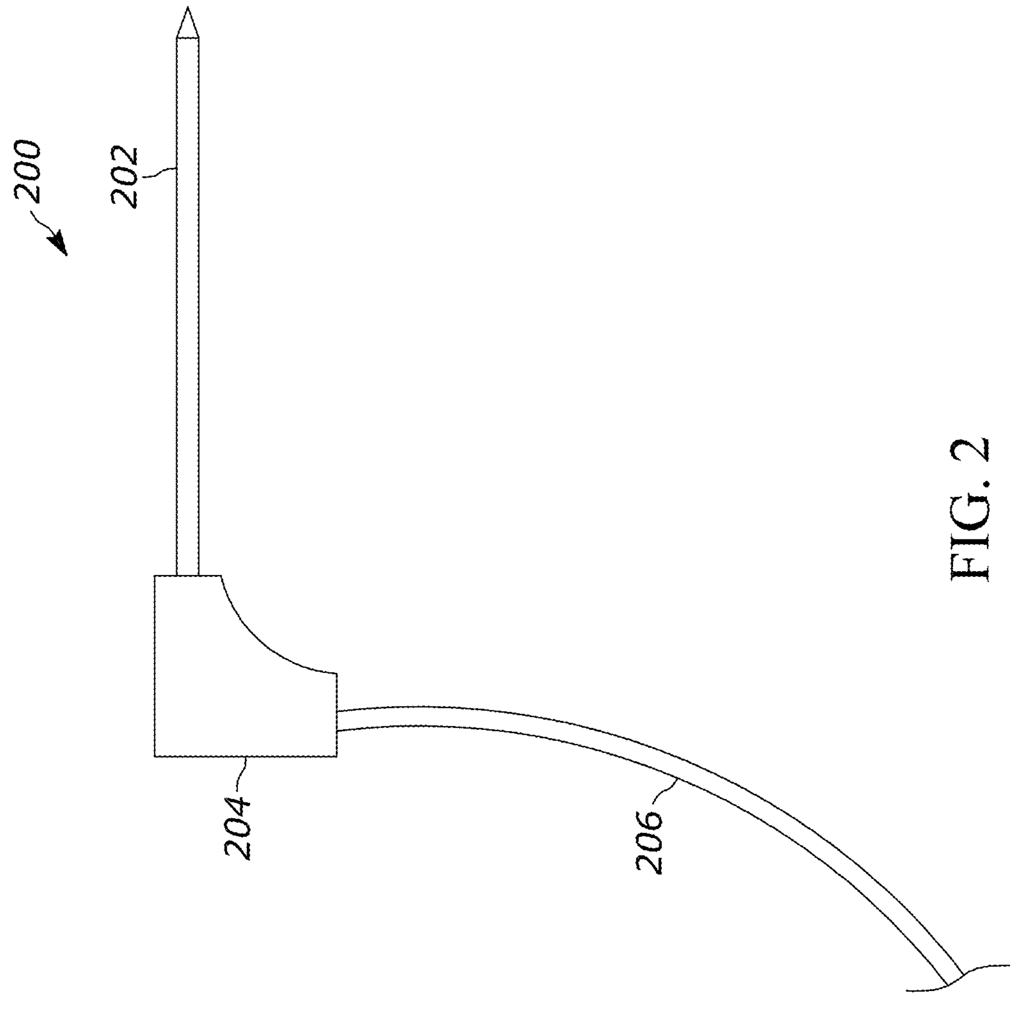
FIG. 2 is an example microwave ablation probe in accordance with some embodiments of the present disclosure

Referring now to FIG. 2, an example ablation probe 200 is shown. The ablation probe 200 may be used with the microwave ablation apparatus 100 previously described. The ablation probe 200 may include a needle 202, a handle 204, and a supply cable 206. The ablation probe 200 may be a disposable or single-use probe that is used during a single procedure or for a single patient. In other examples, the ablation probe 200 (or portions of the ablation probe 200) may be re-used.

The needle 202 of the ablation probe 200 may be an elongated member that maybe inserted into a patient at or near the target tissue. The needle 202 may be a metal, fiberglass, composite, alloy or other rigid material. The needle 202 may be cylindrical and pointed. The needle 202 may be hollow such that various elements are positioned inside the needle 202. For example, a power line and an antenna may be located inside needle 202. The power line may be positioned inside the needle 202 to deliver a power signal from a microwave generator to the antenna. Coolant lines may also be positioned inside the needle to deliver coolant to a distal end of the needle 202. The coolant may be used to control a temperature of the needle 202 and/or to control a size and shape of the ablation zone that may be created at the distal end of the needle 202.

The handle 204 may connect and/or operably couple aspects of the ablation probe 200 that are provided from the supply cable 206 to the needle 202. The supply cable 206 may include a power line that delivers the power signal from the microwave generator. The supply cable 206 may also include a coolant supply line and a coolant return line. The coolant supply line may deliver coolant to the needle 202 and the coolant return line may convey the coolant away from the needle 202 after it has been used to cool the needle 202. The supply cable 206 may also include one or more wires that may be provide signals from one or more temperature sensors, thermocouples, flow sensors, or other sensors that may provide information regarding operating characteristics of the ablation probe 200.

The supply cable 206 may be an elongated tube or conduit and each of the power line, the coolant supply line, the coolant return line, and other wires and lines may extend within an outer shell of the supply cable 206. A length of the supply cable 206 may allow a user of the ablation probe 200 to position the needle 202 of the ablation probe 200 as desired and to allow the patient to be moved in and/or out of an imaging device during a treatment. For example, a location of the needle 202 may be determined using CT, MRI, Ultrasound, or other imaging devices before, during, or after treatment is performed. Thus, the supply cable 206 may be sufficiently long to allow these diagnostic procedures to be performed. In some examples, the supply cable 206 is at least 12 feet in length. In other examples, the supply cable 206 is at least 10 feet in length. In other examples, other lengths may be used.

The handle 204 may connect and/or operably couple the supply cable 206 to the needle 202. The power signal, the coolant, and/or sensor signals may be conveyed or delivered from the supply cable 206 to the needle 202 through the handle 204. The handle 204 may include a housing that may enclose various aspects such as fluid connections, electrical connections, electrical components, and the like. The handle 204 may be configured to orient the needle 202 in a desired alignment relative to the longitudinal axis of the supply cable 206. In the example shown, the handle 204 is a right-angle handle. The handle 204 orients the needle 202 at about 90 degrees (or substantially perpendicular) to the longitudinal axis of the supply cable 206. In other examples, the handle 204 may orient the needle 202 at a different angle relative to the longitudinal axis of the supply cable 206.

Figure 3:
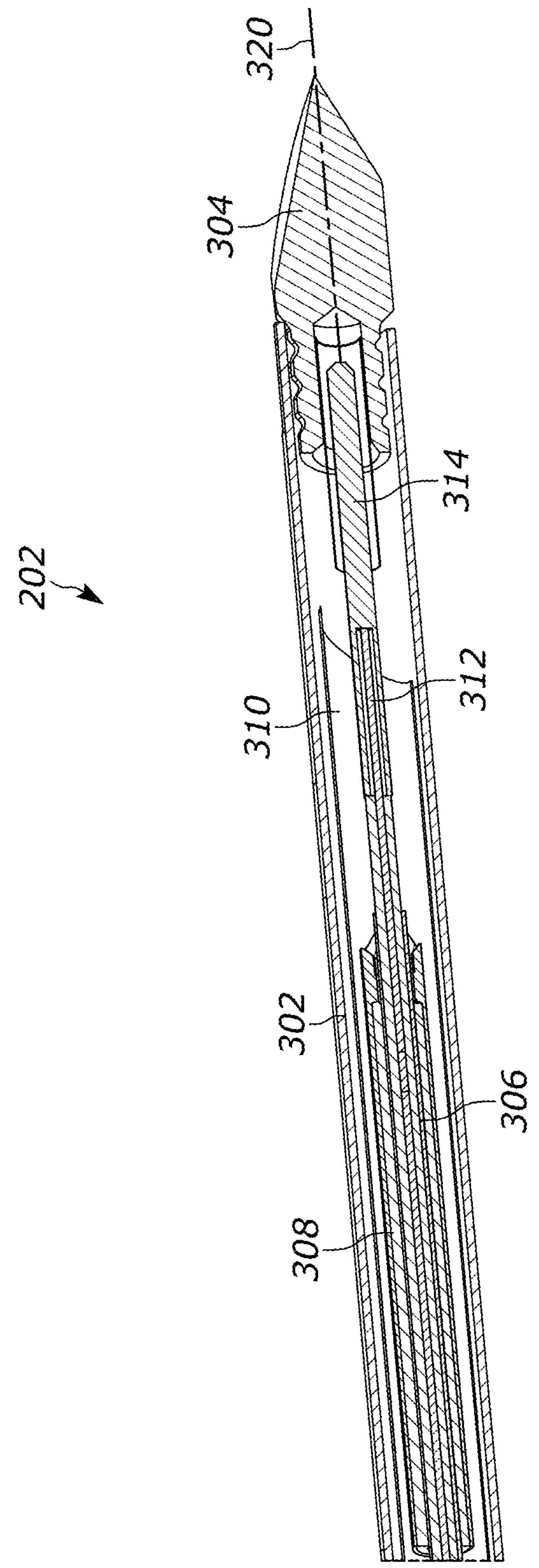
FIG. 3 is a side sectional view of an example tip assembled to a microwave ablation probe of the present disclosure.

Turning now to FIG. 3, an example needle 202 is shown. The needle 202 may include a shell 302, a tip 304, a power cable 306, a choke 308, and a coolant lumen 310. During a treatment, a microwave power signal may travel to an antenna 312 along the power cable 306 from a microwave generator. The power cable 306 may be a coaxial cable that can include an outer conductor and an inner conductor. The current that is passed to the antenna 312 may bounce back or be reflected back (in a direction away from the tip 304) along the outer conductor of the power cable 306. This back current is undesirable because the back-current may cause the ablation zone that is created at the needle 202 to become elongated or have a tear-drop shape rather than being more spherical in shape. The elongated ablation zone may radiate or heat healthy tissues adjacent or near the target tissues. It is desirable, therefore, to prevent and/or minimize distortions that may occur to the size and/or shape of the ablation zone due to reflected to back-current.

The choke 308 may be provided in the needle 202 to prevent, reduce, or minimize back-current that travels back along the power cable 306 in a direction away from the tip 304. The choke 308, as further described below, may include a conductive outer casing that can be electrically coupled to the outer conductor of the power cable 306 to limit, reduce, and/or minimize current that is reflected back along an outer surface of the power cable 306 away from the antenna 312.

The needle 202 may be elongated in a longitudinal or axial direction along axis 320. The various elements of the needle 202 may be concentrically positioned about the axis 320. The shell 302 may be the outermost member of the needle 202 and may be a hollow cylindrical tube that defines an inner cavity. The outer surface of the shell 302 may have a smooth profile to facilitate insertion of the needle 202 into a patient at the target tissue. The tip 304 may be positioned at the distal end of the shell 302 and may be pointed to further facilitate insertion and positioning of the needle 202.

The shell 302 can be made of multiple materials joined together. A first portion of the shell 302 may be made of a stainless steel or other relatively rigid material to provide structure to the needle 202. A second portion located at or near a distal end of the shell may be made of a non-conductive material such as a plastic, fiberglass, ceramic, composite or other non-metallic material. The second portion is made of suitable non-conductive material so as to allow RF energy to be conveyed from the antenna 312 through the shell 302. The end portion may, therefore, be located at a portion of the needle 202 at or near the antenna 312 which is typically located at or near the tip 304.

The cable 306 may be positioned as the innermost element of the needle 202 and may be positioned in a center of the needle along the axis 320. The cable 306 is configured to deliver a suitable current from a microwave generator (not shown) to cause microwave energy (or other RF energy) to be emitted from the antenna 312. The cable 306 can be a coaxial cable that includes a center conductor and an outer conductor. The center conductor may be positioned at a central axis of the cable 306. The outer conductor may be separated from the inner conductor and be configured as a cylinder of conductive material positioned radially outward of the inner conductor along the length of the cable 306.

The antenna 312 may be positioned at a distal end of the cable 306 at or near the tip 304 of the needle 202. The antenna 312 can be configured in any suitable manner such as monopole antenna or a dipole antenna. While one type or configuration of the antenna 312 may be shown in the figures, it should be appreciated that other types or configurations can also be used. As previously described, the antenna 312 is configured to emit RF or microwave energy to heat tissue that is located at or near the antenna 312. In this manner, the needle 202 can generate an ablation zone that is generally located around the antenna 312 at or near the tip 304 of the needle 202. The end of the antenna 312 may be supported by a ferrule 314. The ferrule 314 may be a cylindrical elongated member that includes an inner hole positioned at the center. The antenna 312 may be received into the inner hole of the ferrule. The antenna 312 may be supported in a central location in the shell 302 by the ferrule 314. The ferrule 314 may be coupled to the cable 306 and/or the antenna 312 and be supported on an opposite end at the tip 304. The ferrule 314 may position and maintain the antenna 312 in a desired position radially at the center or axis of the shell 302. The ferrule 314 may also position and maintain the antenna 312 in a desired axial position relative the tip 304.

When in use, the energy of the antenna 312 and current reflected along the outer conductor of the cable 306 may cause the needle 202 to increase in temperature. The heating of the needle 202 may cause the heating zone to become elongated in an axial or longitudinal direction of the needle 202. The elongated heating zone may have an elliptical or teardrop shape, for example. In addition, if the exterior surface of the shell 302 increases in temperature, the tissue in contact with the shell 302 may stick to the shell 302. When the needle 202 is retracted after treatment, the tissue may tear resulting in tearing and/or bleeding that is undesirable. To prevent undesirable heating of the needle 202 and/or to maintain a more spherical ablation zone shape, the needle 202 may include a cooling system to actively cool the needle 202 during operation.

In this example, the needle 202 includes the coolant lumen 310. The coolant lumen 310 can be located between the cable 306 and the shell 302. Thus, the coolant lumen 310 can be located radially outward of the cable 306 and radially inward of the shell 302. The coolant lumen 310 extends longitudinally into the needle 202 along the central axis 320 with a terminating end of the coolant lumen 310 being positioned at or near the antenna 312.

The coolant lumen 310 is configured to deliver a cooling fluid toward the tip 304 of the needle 202. While not shown, the cooling system can include a source of cooling fluid and/or a suitable pump that can deliver a flow of cooling fluid in the interior of the coolant lumen 310 toward the tip 304 of the needle 202. The cooling fluid may return to the source of the cooling fluid or be exhausted or otherwise deposited to another location. During operation, the cooling fluid can flow in a flow path in which the cooling fluid is delivered to the needle in an input channel defined by an interior surface of the cooling tube and an exterior surface of the cable 306. The cooling fluid may flow away from the tip 304 in a return channel defined by an exterior or outer surface of the coolant lumen 310 and an interior surface of the shell 302. The cooling fluid may be any suitable flowable cooling liquid or gas such as water, saline, carbon dioxide gas, or the like.

Figure 4:
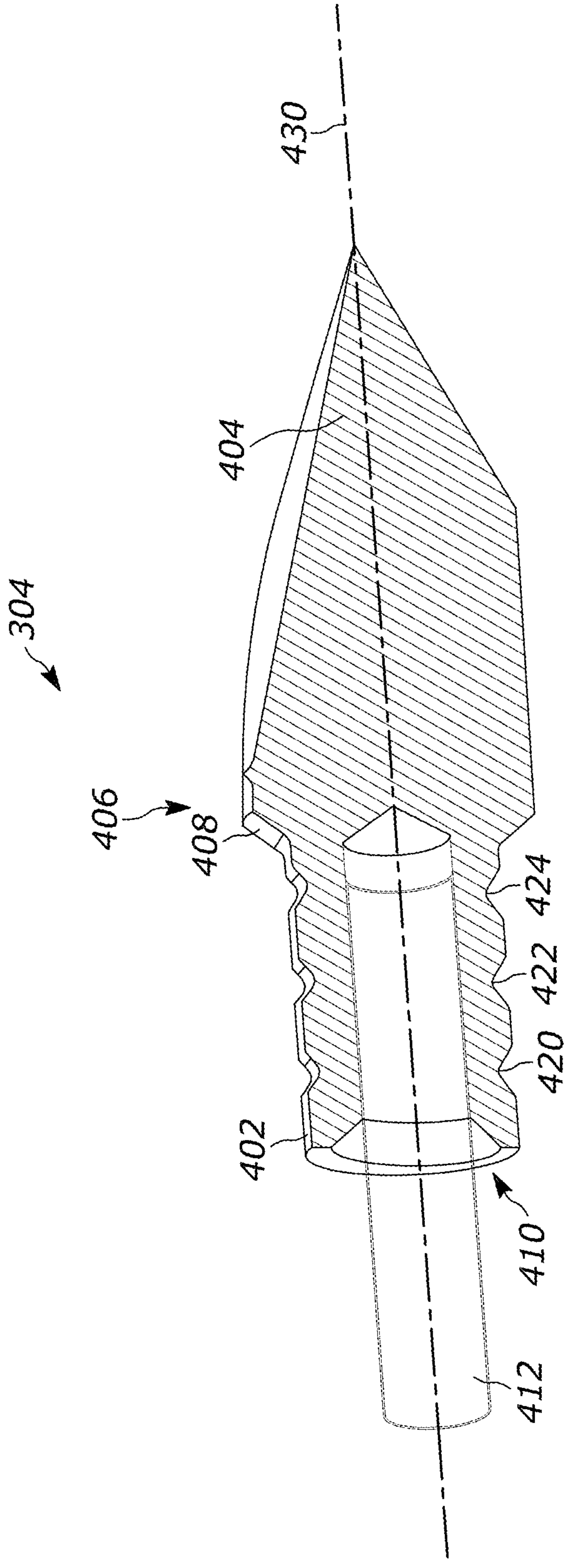
FIG. 4 is a side sectional view of the example tip of FIG. 3.
Figure 5:
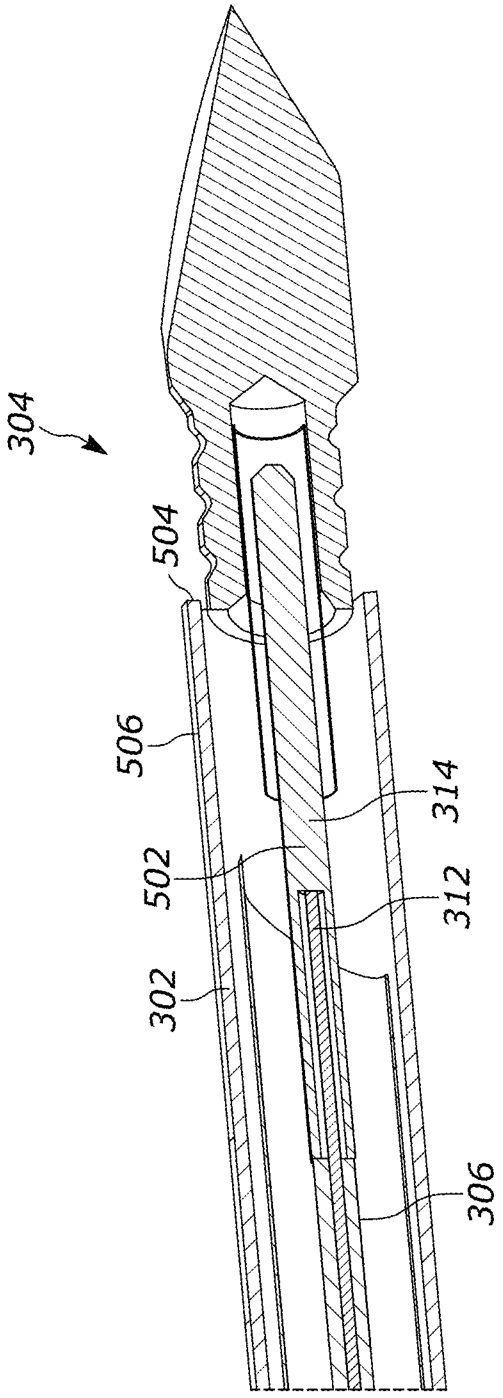
FIG. 5 is a side sectional view of the example tip of FIG. 4 being assembled to a microwave ablation probe.

Referring now to FIGS. 4 and 5, an example probe tip 304 is shown. The probe tip 304 may include a post portion 402 and an insertion portion 404. The post portion 402 may be received into a distal end 506 of the shell 302 of the needle 202. The post portion 402 may nest inside an inner surface of the shell 302. The post portion 402 may be joined to the shell 302 to secure the tip 304 in position relative to the shell 302. A suitable glue, adhesive, epoxy or other joining material may be used to secure the post portion 402 in the shell 302. In one example, a UV-curable adhesive may be used.

The post portion 402 may have a cylindrical shape to fit inside the inner diameter of the shell 302. The outer diameter of the post portion 402 may be smaller than the inner diameter of the shell 302. In some examples, the adhesive or other joining material may be applied to the post portion 402 and then the post portion 402 may be inserted into the distal end 506 of the shell 302. The joining material may be wiped, scraped, or otherwise displaced during the insertion of the post portion 402 into the shell 302. In some instances, the joining material may not be distributed around the exterior surface of the post portion 402 and there may be a leakage path from outside the shell 302 and tip 304 to the interior of the needle 202. In other instances, the joining material may be squeezed during insertion such that the joining material may be deposited on other elements inside the needle 202. For example, the joining material may be squeezed such that it runs off the end of the post portion 402 and drips or otherwise is deposited on the antenna 312 or the ferrule 314. This may lead to the antenna 312 or ferrule 314 being displaced from the centered position in the shell 302. If the antenna 312 is displaced, the size and/or shape of the ablation zone may be affected.

The post portion 402 may include one or more grooves positioned circumferentially at the outer surface. In the example shown, the post portion 402 includes a first groove 420, a second groove 422, and a third groove 424. Each of the first groove 420, the second groove 422, and the third groove 424 may be formed around the circumference of the post portion 402. The first groove 420, the second groove 422, and the third groove 424 may be axially separated from each other. In other examples, the tip 304 may include more or less than three grooves and/or the grooves may be spaced at different or varying intervals along the surface of the post portion 402.

The first groove 420, the second groove 422, and the third groove 424 may allow for the adhesive or other joining material to occupy each of the grooves. In this manner, the joining material is not displaced or removed from the post portion 402 during insertion of the tip 304 into the shell 302. Furthermore, since each of the grooves extends around a circumference or periphery of the post portion 402, the joint that is created can be uninterrupted around a periphery of the post portion 402. The joining material may also be moved or pushed into one of the grooves rather than being moved or pushed off the post portion 402 during installation of the tip 304.

The tip 304 may also include an insertion portion 404. The insertion portion 404 may remain exposed after installation of the tip 304. The insertion portion 404 may be tapered and gradually reduce in width or diameter and may terminate at a point. The insertion portion 404 may be used to pierce or travel through tissue of the patient during insertion of the microwave ablation probe 200.

The insertion portion 404 may include shoulder 406 at which the tip 304 transitions from the post portion 402 to the insertion portion 404. The shoulder 406 may include a seating surface 408 that may contact an end surface 504 of the shell 302 when the tip 304 is installed into the shell 302. In the example shown, the seating surface 408 may be angled at an oblique angle relative to the axis 430 of the tip 304. The seating surface 408 may angled such that it is sloped away from the post portion 402. The seating surface 408, with this configuration, may funnel and/or guide the tip 304 into a centered position in the shell 302. The seating surface 408 may act as a self-centering feature of the tip 304. When the tip 304 is inserted into the shell 302, the angled seating surface 408 may shift the location of the tip 304 relative to the shell 302 when the seating surface 408 contacts the end surface 504 of the shell 302. This centering feature aligns the center axis 430 of the tip 304 with the center axis of the shell 302.

The tip 304 may also include a bore 410 that extends into the post portion 402. The bore 410 may be sized and shaped to allow the ferrule 314 to be positioned inside the bore 410. The tip 304 may be inserted into the shell 302 when the cable 306, antenna 312, and ferrule 314 have been previously installed. Upon insertion of the tip 304 into the shell 302 the ferrule 314 may be guided into the bore 410. This may assist in maintaining the antenna 312 in a centered position in the shell 302.

The tip 304 may also include a tube 412 that may be positioned in the bore 410. The tube 412 may have an outer diameter that is smaller than an inner diameter of the bore 410 so that the tube 412 may be inserted into the bore 410. The tube 412 may have a length so that one end of the tube 412 extends out of the bore 410 and remains exposed. As the tip 304 is installed into the shell 302, the tube 412 may be aligned with the ferrule 314 and may assist with guiding the ferrule 314 into the bore 410.

The tube 412 may also cover or shield a portion ferrule 314 that may be located at or near the end of the post portion 402. When the tip 304 is installed into the shell 302, an adhesive or other joining material may be deposited on the exterior surface of the post portion 402. As the tip 304 is installed into the shell 302, some of the adhesive or other joining material may be squeezed or pushed off the post portion 402. In examples that do not include tube 412, the excess adhesive or other joining material may fall onto the ferrule 314 or the antenna 312. The adhesive may bind the ferrule or antenna 312 into an undesirable orientation that is not centered in the shell. This may cause a skew or distortion to the ablation zone. It is desirable, therefore, to include the tube 412 so that the ferrule 314 and/or the antenna 312 is shielded from excess adhesive or other joining material that may fall or flow from the post portion 402.

The tip 304 may be integrally formed such that the post portion 402 and the insertion portion 404 form a unitary element. The tip 304 is suitably rigid to be inserted through body tissues to position the tip 304 (and antenna 312) in a desired position relative to target tissue. The tip 304 should also be made of a suitable material so as to not interfere with the emission of microwaves during the ablation treatment. In some examples, the tip 304 may be made of a suitable ceramic material.

The tip 304 may be produced using one or more machining operations to create the shape and features previously described. In such examples, a cylindrical rod of ceramic material may be machined to create the post portion 402, the grooves 420, 422, 434, and the bore 410. The tapered insertion portion 404 and the seating surface 408 may also be machined into the tip 304. The machining of the tips 304 may be a time consuming and/or expensive process relative to other techniques. In one alternate process, the tip 304 may be injection molded and made of a ceramic material. A mold may be prepared to include a profile of the tip 304. In such examples, the insertion portion 404 may include a conical smooth tapered profile. In still other examples, a combination of processes may be used to create the tip 304.

The following is a list of non-limiting illustrative embodiments disclosed herein:

Illustrative embodiment 1: A microwave ablation probe tip comprising: a post portion configured to be received in an ablation probe needle, the post portion comprising one or more annular grooves; and an insertion portion comprising a shoulder at which the insertion portion is connected to the post portion, wherein the insertion portion tapers in a direction away from the shoulder.

Illustrative embodiment 2: The microwave ablation probe tip of illustrative embodiment 1, wherein each of the one or more annular grooves extends circumferentially around an outer surface of the post portion.

Illustrative embodiment 3: The microwave ablation probe tip of illustrative embodiment 1 or 2, wherein the one or more annular grooves comprises a first groove, a second groove, and a third groove axially spaced apart from each other.

Illustrative embodiment 4: The microwave ablation probe tip of any of illustrative embodiments 1 to 3, wherein the insertion portion comprises a seating surface configured to contact an end surface of the ablation probe needle, the seating surface angled relative to the end surface of the ablation probe needle.

Illustrative embodiment 5: The microwave ablation probe tip of illustrative embodiment 4, wherein the seating surface is angled in a direction away from the post portion.

Illustrative embodiment 6: The microwave ablation probe tip of any of illustrative embodiments 4 or 5, wherein the seating surface is positioned radially outward of an outer surface of the post portion.

Illustrative embodiment 7: The microwave ablation probe tip of any of the illustrative embodiments 1 to 6, wherein the insertion portion terminates at a point.

Illustrative embodiment 8: The microwave ablation probe tip of any of illustrative embodiments 1 to 7, wherein the insertion portion comprises a conical shape.

Illustrative embodiment 9: The microwave ablation probe tip of any of illustrative embodiments 1 to 8, wherein the post portion includes a center bore.

Illustrative embodiment 10: The microwave ablation probe tip of any of illustrative embodiments 1 to 9, further comprising a tube positioned in the center bore and extending out of the center bore in a direction away from the insertion portion.

Illustrative embodiment 11: The microwave ablation probe tip of illustrative embodiment 10, wherein the tube is configured to receive a microwave antenna therein.

Illustrative embodiment 12: A microwave ablation probe comprising: a shell defining an axially extending inner cavity; a cable positioned in the inner cavity and comprising a microwave antenna; and a tip connected at a distal end of the shell, the tip comprising a post portion received inside the distal end of the shell and an insertion portion connected to the post portion and extending away from the distal end of the shell, the post portion comprising one or more annular grooves.

Illustrative embodiment 13: The microwave ablation probe of illustrative embodiment 12, wherein the tip comprises a seating surface contacting the end surface of the distal end of the shell, the seating surface oriented at an oblique angle relative to an axis of the shell.

Illustrative embodiment 14: The microwave ablation probe of illustrative embodiment 13, wherein the seating surface is angled in a direction away from the post portion.

Illustrative embodiment 15: The microwave ablation probe of any of illustrative embodiments 12 to 14, wherein the insertion portion comprises a tapered outer surface terminating at a point.

Illustrative embodiment 16: The microwave ablation probe of any of illustrative embodiments 12 to 15, wherein the post portion includes a center bore.

Illustrative embodiment 17: The microwave ablation probe of illustrative embodiment 16, further comprising a ferrule positioned over the antenna, the ferrule extending in an axial direction from the antennae and at least a portion of the ferrule received inside the center bore.

Illustrative embodiment 18: The microwave ablation probe of illustrative embodiment 17, wherein the tip comprises a tube positioned in the center bore and extending out of the center in a direction away from the insertion portion, the at least a portion of the ferrule positioned inside the tube.

Illustrative embodiment 19: The microwave ablation probe tip of any of illustrative embodiments 1 to 11, wherein the post portion and the insertion portion are integrally formed from a ceramic material using an injection molding process.

Illustrative embodiment 20: The microwave ablation probe of any of illustrative embodiments 12 to 19, wherein the post portion and the insertion portion of the tip are integrally formed from a ceramic material using an injection molding process.

Illustrative embodiment 21: A microwave ablation apparatus comprising: an ablation console comprising a microwave generator; and a microwave ablation probe comprising: a shell defining an axially extending inner cavity; a cable positioned in the inner cavity and comprising a microwave antenna; and a tip connected at a distal end of the shell, the tip comprising a post portion received inside the distal end of the shell and an insertion portion connected to the post portion and extending away from the distal end of the shell, the post portion comprising one or more annular grooves.

The foregoing is provided for purposes of illustrating, explaining, and describing embodiments of these disclosures. Modifications and adaptations to these embodiments will be apparent to those skilled in the art and may be made without departing from the scope or spirit of these disclosures.

What is claimed is:

1. A microwave ablation probe tip comprising:

a post portion configured to be received in an ablation probe needle, the post portion comprising:

a cylindrical body defining:

one or more annular grooves disposed circumferentially on an outer surface of the cylindrical body; and a center bore extending through the cylindrical body;

a tube positioned in the center bore;

an insertion portion connected to the post portion, the insertion portion comprising:

an insertion portion body tapering to terminate at a point; and a shoulder at which the insertion portion is connected to the post portion, wherein the insertion portion body tapers in a direction away from the shoulder, wherein the tube extends away from the center bore in a direction away from the insertion portion; and a ferrule, wherein at least a portion of the ferrule is received inside the center bore and the tube shields a portion of the ferrule.

2. The microwave ablation probe tip of claim 1, wherein the one or more annular grooves comprises a first groove, a second groove, and a third groove axially spaced apart from each other.

3. The microwave ablation probe tip of claim 1, wherein the insertion portion comprises a seating surface configured to contact an end surface of the ablation probe needle, the seating surface angled relative to the end surface of the ablation probe needle.

4. The microwave ablation probe tip of claim 3, wherein the seating surface is angled in a direction away from the post portion.

5. The microwave ablation probe tip of claim 3, wherein the seating surface is positioned radially outward of an outer surface of the post portion.

6. The microwave ablation probe tip of claim 1, wherein the insertion portion comprises a conical shape.

7. The microwave ablation probe tip of claim 1, wherein the tube is configured to receive a microwave antenna therein.

8. The microwave ablation probe tip of claim 1, wherein the post portion and the insertion portion are integrally formed from a ceramic material using an injection molding process.

9. A microwave ablation probe comprising:

a shell defining an axially extending inner cavity;

a cable positioned in the inner cavity and comprising a microwave antenna;

a tip connected at a distal end of the shell, the tip comprising a post portion received inside the distal end of the shell and an insertion portion connected to the post portion and extending away from the distal end of the shell, the post portion comprising one or more annular grooves; and a ferrule positioned over the antenna, the ferrule extending in an axial direction from the antenna and at least a portion of the ferrule received inside the center bore.

10. The microwave ablation probe of claim 9, wherein the tip comprises a seating surface contacting the end surface of the distal end of the shell, the seating surface oriented at an oblique angle relative to an axis of the shell.

11. The microwave ablation probe of claim 10, wherein the seating surface is angled in a direction away from the post portion.

12. The microwave ablation probe of claim 9, wherein the insertion portion comprises a tapered outer surface terminating at a point.

13. The microwave ablation probe of claim 9, wherein the post portion includes a center bore.

14. The microwave ablation probe of claim 9, wherein the post portion and the insertion portion of the tip are integrally formed from a ceramic material using an injection molding process.

15. A microwave ablation apparatus comprising:

an ablation console comprising a microwave generator; and a microwave ablation probe comprising:

a shell defining an axially extending inner cavity;

a cable positioned in the inner cavity and comprising a microwave antenna; and a tip connected at a distal end of the shell, the tip comprising:

a post portion received inside the distal end of the shell, the post portion comprising:

a cylindrical body defining:

one or more annular grooves disposed circumferentially on an outer surface of the cylindrical body; and a center bore extending through the cylindrical body;

a tube positioned in the center bore;

an insertion portion connected to the post portion and extending away from the distal end of the shell, the insertion portion comprising:

an insertion portion body tapering to terminate at a point; and a shoulder at which the insertion portion is connected to the post portion, wherein the insertion portion body tapers in a direction away from the shoulder, wherein the tube extends away from the center bore in a direction away from the insertion portion; and a ferrule, wherein at least a portion of the ferrule is received inside the center bore and the tube shields a portion of the ferrule.

* * * * *